US006933379B2

(12) United States Patent
Van Kuppevelt et al.

(10) Patent No.: US 6,933,379 B2
(45) Date of Patent: Aug. 23, 2005

(54) METHOD FOR LINKING NUCLEIC ACIDS AND/OR GLYCOSAMINOGLYCANS TO POLAR/HYDROPHILIC MATERIALS

(75) Inventors: Antonius H. M. S. M. Van Kuppevelt, Nijmegen (NL); Jacobus Henricus Veerkamp, Nijmegen (NL); Thiemo Arnim Blank, Plankstadt (DE)

(73) Assignee: Angiomed GmbH & Co. Medizintechnik KG, Karlsruhe (DE)

(*) Notice: Subject to any disclaimer, the term of this patent is extended or adjusted under 35 U.S.C. 154(b) by 0 days.

(21) Appl. No.: 10/258,093

(22) PCT Filed: Mar. 30, 2001

(86) PCT No.: PCT/EP01/03666

§ 371 (c)(1),
(2), (4) Date: Apr. 4, 2003

(87) PCT Pub. No.: WO01/81925

PCT Pub. Date: Nov. 1, 2001

(65) Prior Publication Data

US 2003/0166597 A1 Sep. 4, 2003

(30) Foreign Application Priority Data

Apr. 19, 2000 (GB) .............................................. 0009771

(51) Int. Cl.$^7$ ........................ C07H 21/00; C07H 21/02; C07H 21/04; G01N 15/06; C12N 1/08
(52) U.S. Cl. ................ 536/25.4; 536/25.41; 536/25.42; 422/68.1; 435/270
(58) Field of Search ........................... 536/25.4, 25.41, 536/25.42; 422/68.1; 435/270

(56) References Cited

U.S. PATENT DOCUMENTS

| 5,356,433 A | | 10/1994 | Rowland et al. |
| 5,804,684 A | * | 9/1998 | Su .............................. 536/25.4 |
| 5,955,588 A | * | 9/1999 | Tsang et al. .................. 536/21 |
| 6,180,769 B1 | | 1/2001 | Van Kuppevelt et al. |
| 2001/0041332 A1 | | 11/2001 | Hillebrand et al. |

FOREIGN PATENT DOCUMENTS

| EP | 0389063 A2 | 9/1990 |
| WO | WO 96/18905 A1 | 6/1996 |
| WO | WO 00/34463 A1 | 6/2000 |

OTHER PUBLICATIONS

Lide, D.E., *Handbook of Chemistry and Physics*, 74th Edition, CRC Press, pp. 12–143 to 12–146.
Schuerch, H.U., "Certain physical properties and applications of Nitinol," NASA CR–1232, NASA (1968).
Duerig, T.W., Pelton, A.R. and Stöckel, D., "Superelastic Nitinol for Medical Devices," *Medical Plastics and Biomaterials*, Mar./Apr. (1997).

* cited by examiner

*Primary Examiner*—Jezia Riley
(74) *Attorney, Agent, or Firm*—Kirkpatrick & Lockhart Nicholson Graham LLP

(57) ABSTRACT

The invention relates to a method for linking nucleic acid and/or glycosaminoglycan or glycosaminoglycan mimetics to a polar/hydrophilic material, characterized by contacting a nucleic acid and/or glycosaminoglycan and a polar/hydrophilic material with each other in the presence of a solution being 20 to 100 percent saturated with a non-chaotropic salt and removing said solution from the nucleic acid and/or glycosaminoglycan—polar/hydrophilic material.

64 Claims, 3 Drawing Sheets

METHOD FOR LINKING NUCLEIC ACIDS AND/OR GLYCOSAMINOGLYCANS TO POLAR/HYDROPHILIC MATERIALS

CROSS REFERENCE TO RELATED APPLICATIONS

This application is based on International Patent Application No. PCT/EP01/03666, filed Mar. 30, 2001, having an International Publication No. WO 01/81925 A1 and an International Publication Date of Nov. 1, 2001, and claims priority under 35 U.S.C. §119 to British Patent Application No. GB 0009771.7, filed Apr. 19, 2000.

BACKGROUND

The invention relates to a method for linking nucleic acids and/or glycosaminoglycans and/or glycosaminoglycan mimetics to polar/hydrophilic materials.

Nucleic acids such as deoxyribonucleic acid (DNA) and ribonucleic acid (RNA) and glycosaminoglycans (GAG) play a crucial part in cell functioning. DNA typically encodes proteins, RNA is typically an intermediate in protein synthesis and glycosaminoglycans play an important role in fundamental processes such as growth, differentiation and blood coagulation.

Nucleic acids such as DNA and RNA consist of covalently linked chains of deoxyribonucleotides (DNA) or covalently linked chains of ribonucleotides (RNA). Each nucleotide in DNA and RNA contains three characteristic components (1) a nitrogenous heterocyclic base which is a derivative of either pyrimidine or purine and (2) a pentose sugar and (3) a molecule of phosphoric acid that forms a negatively charged "backbone".

Glycosaminoglycans are polysaccharide molecules made up of disaccharide repeating units containing a derivative of an amino sugar, either glucosamine or galactosamine wherein at least one of the sugars in a disaccharide unit has a negatively charged carboxylate or sulfate group. Glycosaminoglycans are heterogeneous in this respect and can contain 1 to 4 negative charges per disaccharide.

Nucleic acids and glycosaminoglycans can both be viewed as polymeric molecules with a "backbone" having a series of negative charges at neutral pH.

As a result of the development of molecular biological techniques, nucleic acids play an increasingly large part in the analysis of biological material. Fragments of DNA or RNA that are specific for example for causative organisms of disease (bacteria, viruses, etc.) can be used for detection of these organisms and diagnosis of hereditary diseases also occurs at nucleic acid level. Aside from the diagnostic importance of DNA/RNA, nucleic acids are also often employed for synthesis of specific proteins via recombinant DNA techniques and PCR (polymerase chain reaction).

Heparin has been demonstrated to have strong anticoagulant properties and is useful in the production of medical devices where it may serve to prevent the binding of thrombocytes (blood platelets) to said medical devices and inhibit the formation of neointima formation (intimal hyperplasia).

Devices which are coated with nucleic acids and/or glycosaminoglycans for use in diagnostics or medicine should be able to bind a significant amount of nucleic acids and/or glycosaminoglycans in a tight association so that said nucleic acids and/or glycosaminoglycans are not significantly lost from the surfaces of devices coated with or linked to these macromolecules.

EP 797 778 relates to a method for preparing non-proteinaceous strongly negatively charged macrobiomolecules which are linked to plastic. Plastics may be considered as high molecular weight materials that contain synthetic or semisynthetic organic substances made by polymerization or condensation or derived from a natural material by chemical treatment that are molded, cast, extruded, drawn or laminated under various conditions. The method described in EP 797 778 is based on the finding that negatively charged molecules can be bound to apolar plastic surfaces like polystyrene using high salt conditions. The fact that the binding only occurs (is strongly increased) at very high salt concentrations strongly suggests that hydrophobic interactions are the basis of the bonding. The mechanism of operation is described in this patent application as resulting from the fact that the salt removes the water coat around the negatively charged molecules and shields the negative charges such that the interaction with apolar plastic, for example polystyrene, is strongly improved.

Hydrophobic interactions are of course expected to be much stronger to non-polar hydrophobic surfaces like plastics such as polystyrene than to polar/hydrophilic surfaces.

A number of materials used for diagnostic tests and medical devices are polar/hydrophilic materials. It should be reasoned therefore that binding of charged biomolecules such as nucleic acids and/or glycosaminoglycans to these polar/hydrophilic materials occurs through electrostatic interactions, and that promoting hydrophobic interactions would be of no advantage.

An object of the present invention is to provide a method for strongly linking nucleic acids and/or glycosaminoglycans to materials useful for diagnostic tests and assays and medical devices.

A further object of the present invention is to provide materials strongly linked to nucleic acids and/or glycosaminoglycans as well as devices comprising or consisting of materials strongly linked to nucleic acids and/or glycosaminoglycans

DETAILED DESCRIPTION

SUMMARY OF THE INVENTION

Figure 1:
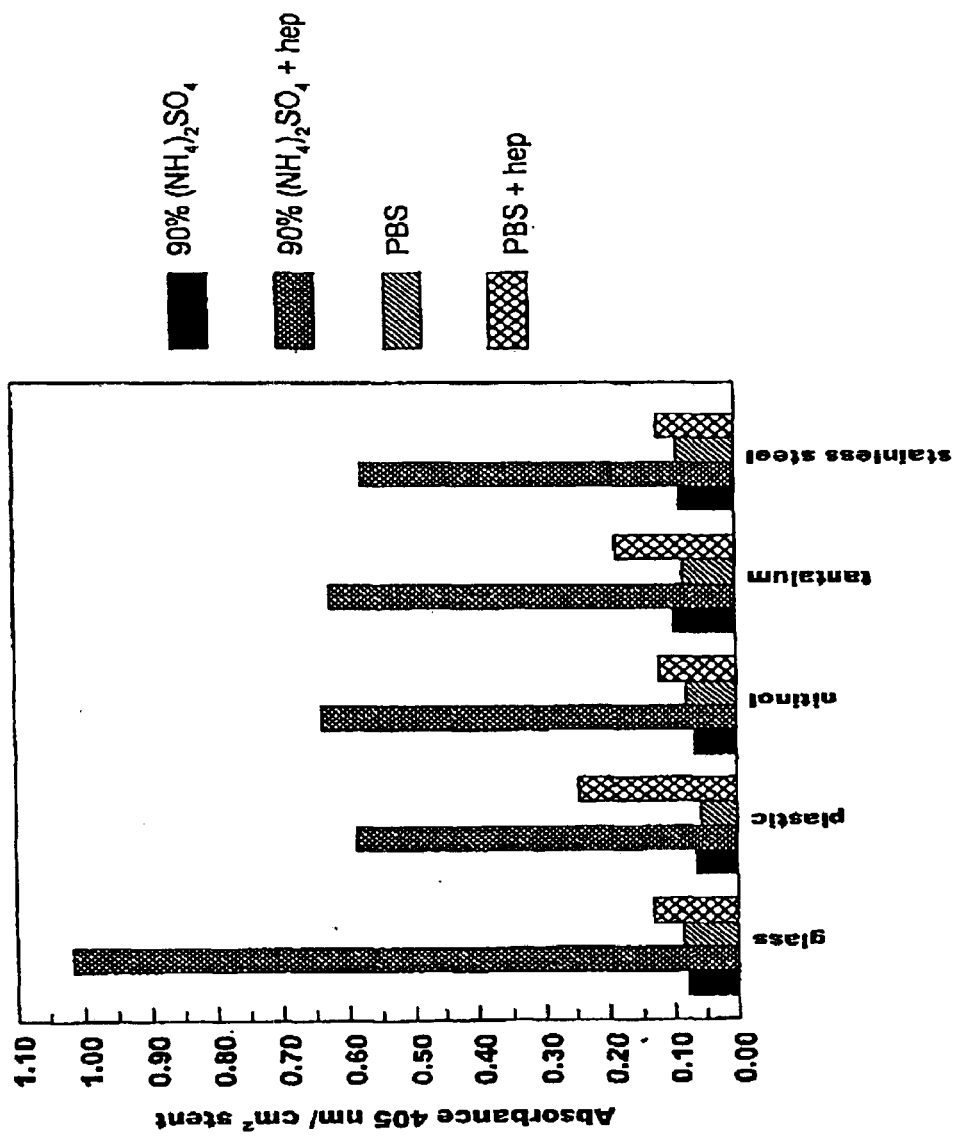
FIG. 1. Coating of various materials with heparin.

It has been surprisingly and unexpectedly found that increasing hydrophobic environment of nucleic acids and/or glycosaminoglycans and polar/hydrophilic materials results in a dramatic increase in the amount of nucleic acid and/or glycosaminoglycan that can be bound to such materials. It has been demonstrated that a considerable increase in nucleic acid and/or glycosaminoglycan binding occurs to polar/hydrophilic materials when using the method of the invention. Thus, the subject invention comprises an inexpensive, efficient and reliable method to directly bind nucleic acid and/or glycosaminoglycan to polar/hydrophilic materials.

As stated above, nucleic acids such as DNA and RNA consist of covalently linked chains of deoxyribonucleotides (DNA) or covalently linked chains of ribonucleotides. Each nucleotide in DNA and RNA contains three characteristic components (1) a nitrogenous heterocyclic base which is a derivative of either pyrimidine or purine, (2) a pentose sugar and (3) a molecule of phosphoric acid that forms a negatively charged "backbone". Major nucleotides found in DNA are deoxyadenosine monophosphate (dAMP), deoxyguanosine monophosphate (dGMP), deoxycytidine monophosphate (dCMP) and deoxythymidine monophosphate (dTMP). Major nucleotides found in RNA are adenosine monophosphate (AMP), guanosine monophosphate (GMP), cytidine monophosphate (CMP) and uridine monophosphate (UMP). In addition, inosine monophosphate (IMP) is sometimes incorporated into nucleic acids that can be used in molecular biology such as DNA probes. In addition to the adenine, guanine, cytosine, thymine and uracil bases found in nucleic acids, other minor bases which can be found in nucleic acids include 5,6-dihydrouracil, 1-methyluracil, 3-uracil, 5-hydroxymethyluracil, 2-thiouracil, $N^4$-acetylcytosine, 3-methylcytosine, 5-methylcytosine, 5-hydroxymethylcytosine, 1-methyladenine, 2-methyladenine, 7-methyladenine, $N^6$-methyladenine, $N^6,N^6$-dimethyladenine, $N^6(\Delta^2$-isopentenyl) adenine, 1-methylguanine, 7-methylguanine, $N^2$-methylguanine and $N^2,N^2$-dimethylguanine. Nucleic acids such as DNA and RNA comprising the above mentioned bases as well as derivatives thereof are considered as nucleic acids within the meaning of the present invention. Moreover, individual nucleotides containing the above bases or derivatives thereof are included within the meaning of nucleic acids according to the invention.

The invention also relates to a method for linking naturally occurring or synthetic negatively charged polymers to polar/hydrophilic materials.

As stated above, glycosaminoglycans are polysaccharide molecules comprising disaccharide repeating units containing a derivative of an amino sugar, either glucosamine or galactosamine wherein at least one of the sugars in a disaccharide unit has a negatively charged carboxylate or sulfate group. Glycosaminoglycans are heterogeneous in this respect and can contain 1 to 4 negative charges per disaccharide. Within the meaning of the present invention, glycosaminoglycans include heparin, heparan sulfate, hyaluronate, chondroitin sulfate, dermatan sulfate, chitosan sulfate acharan sulfate and keratan sulfate and derivatives thereof.

Glycosaminoglycan-like mimetics according to the invention are molecules reflecting a charge distribution similar to glycosaminoglycans. Examples are laminarin sulfate, dextran sulfate, pentosan sulfate and suramin.

In addition, molecules according to the invention include the above mentioned molecules which are radioactively labeled at one or more position, preferably with $^{32}P$, $^{35}S$ or $^{3}H$, or bind radioactive molecules or atoms, preferably $^{76}As$, $^{90}Y$, $^{103}Pd$, $^{111}In$, $^{115}Cd$, $^{135}I$, $^{140}La$, $^{153}Sm$, $^{156}Sm$, $^{186}Re$, $^{188}Re$, $^{192}Ir$ and $^{194}Ir$.

Polar/hydrophilic materials according to the invention include metals and metal-based compounds such as metal oxides, metal alloys, oxidized metal alloys, glasses and ceramics.

Metals according to the invention are selected from the group consisting of Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Preferred metals are titanium, tantalum, gold and platinum.

Metal oxides according to the invention are selected from the group consisting of the above listed metals. A preferred metal oxide is titanium oxide.

Metal alloys according to the invention are selected from the group consisting of stainless steels, Ti alloys, Co—Cr alloys and other alloys of the above metals. Preferred metal alloys are nickel-titanium alloys, stainless steels. Most preferably, the metal alloy is a nickel-titanium alloy such as Nitinol® or stainless steel. Oxides of the above alloys are included within the meaning of the above mentioned metal alloys.

Glasses according to the invention include those glasses listed on pages 12–143 to 12–146 in Handbook of Chemistry and Physics, 74$^{th}$ Edition, CRC Press, Ed.: David E. Lide.

Ceramics according to the invention are selected from the group consisting of aluminum oxides, zirconia ceramics, calsium aluminates, hydroxapatites, aluminum-calciumphosphorous oxides, glass fibers and their composites, calcium sulfates, ferric calcium phosphorous oxides, tricalcium phosphate, zinc-calcium phosphorous oxides, zinc sulfate-calcium-calcium phosphorous oxides and the like.

These polar/hydrophilic materials need not be subjected to chemical activation or modification and can thus be applied as such which offers an appreciable advantage over the existing methods. Furthermore, hydrophobic interactions are very stable in hydrophilic (polar) surroundings.

The polar/hydrophilic materials according to the invention can exist as such in any form or exist as a coating on or layer in a material or materials other than the polar/hydrophilic materials according to the invention or comprising different polar/hydrophilic material or materials according to the invention. They can exist as particles, beads, wires, meshes, nets, sheets, tubes, tubules and the like.

The method according to the invention for linking nucleic acid and/or glycosaminoglycan to a polar/hydrophilic material is characterized by contacting a nucleic acid and/or glycosaminoglycan and a polar/hydrophilic material with each other in the presence of a solution being 20 to 100 percent saturated with a non-chaotropic salt and removing said solution.

A person skilled in the art will realize what salts are to be considered chaotropic and non-chaotropic according to the invention. A non-chaotropic salt belonging to the Hofmeister series of salts is used for the solution according to the subject invention. Generally speaking salts capable of salting out proteins are non-chaotropic. In general, the method according to the subject invention will be carried out with a salt capable of salting out proteins. The most non-chaotropic substances are combinations of ions from the left of the Hofmeister series. A non chaotropic salt of a metal from group I or II of the Periodic Table of Elements or a $NH_4$ salt are examples of effective salts. A solution which comprises at least a salt with an anion from the group of halogens comprising chloride and bromide, or the group phosphate, sulfate and acetate is also effective. Of the halogens, chloride is preferred. Salts that are very useful in a method according to the subject invention are NaCl, KCl, $MgCl_2$, $MgSO_4$, $(NH_4)_2SO_4$, $NaH_2PO_4$ and $Ca(AC)_2$. Combinations of any of $SO_4^{2-}$, $H_2PO_4^-$, $CH_3COO^-$ and $Cl^-$ with any of $NH_4^+$, $Cs^+$, $K^+$ and $Na^+$ are also non-chaotropic salts within the meaning of the invention including $(NH_4)_2SO_4 Cs_2SO_4$, $K_2SO_4$, $Na_2SO_4$, $Li_2SO_4$, $(NH_4)_2H_2PO_4$, $Cs_2H_2PO_4$, $K_2H_2PO_4$, $Na_2H_2PO_4$, $Li_2H_2PO_4$, $NH_4CO_2CH_3$, $CsCO_2CH_3$, $KCO_2CH_3$, $NaCO_2CH_3$, $NH_4Cl$, $CsCl$, $KCl$, $NaCl$, $LiCl$, $NH_4Br$, $CsBr$, $KBr$, $NaBr$, and $LiBr$. Any agent capable of increasing the hydrophobic nature of the nucleic acid and/or glycosaminoglycan and the non-plastic material to the same degree as salts from the left of the Hofmeister series as mentioned above can be considered suitable for carrying out the invention if they do not denature the nucleic acid/glycosaminoglycan.

In particular, $(NH_4)_2SO_4$ or NaCl are preferred non-chaotropic salts in the method according to the invention, with $(NH_4)_2SO_4$ being most preferred, because only low amounts of the nucleic acid/glycosaminoglycan to be bound are required for optimal binding.

Preferably, a solution with a degree of saturation of at least 50% is used in the method according to the invention, with more preference for a degree of saturation of at least 60%. Optimal results are obtained with a solution with a degree of saturation between 70–100%, preferably 90–100%. The skilled person will realize that the degree of saturation depends on the temperature of the solution and can adjust the amount of salt in said solution accordingly.

The circumstances will vary depending on the molecule to be linked and a person skilled in the art will know for biomolecules such as DNA, RNA and GAG which pH and which salt concentrations are suitable.

The method according to the subject invention can be carried out in the various embodiments mentioned above at temperatures between 0–100° C., preferably between 2–90° C.

The method according to the subject invention comprises one or more steps after the linkage step for removing the linkage solution. The linked product can be rinsed with water to achieve this. It is also possible to apply a salt solution, a buffered solution, or a buffered solution containing salt, and optionally a detergent for rinsing.

For hybridization research, double stranded DNA may be linked using the method according to the subject invention. The method for linkage of double stranded DNA to a polar/hydrophilic material according to the invention proceeds best in a saturated or nearly saturated, i.e. 90–100% saturated, salt solution in water. A solution of NaCl or $(NH_4)_2SO_4$ is excellent. Good results can be achieved for the linkage step with incubation overnight at 4° C. The bases of the nucleic acids are left available for the hybridization test (base pairing). Carrying out amplification reactions such as PCR belongs to the possibilities as well as uses of the polar/hydrophilic material linked to nucleic acids which additionally contain proteins capable of binding to nucleic acids such as polymerases, transcription factors and the like.

The method in any of the embodiments or combination of embodiments disclosed above is applicable for any diagnostic or medical device wherein nucleic acid and/or glycosaminoglycan need to be immobilized to polar/hydrophilic material. One of the more important areas of application lies in diagnostic methods in which DNA/RNA are involved, in particular for detecting pathogenic organisms with the aid of specific DNA probes by means of hybridization techniques. In addition, the diagnosis of diseases or specific DNA/RNA sequences in which anti-DNA or anti-RNA or anti-GAG antibodies are involved is another possible embodiment. The biological characteristics of GAG can be well used in this manner. The HIV virus for example binds specifically to heparan sulfate (a GAG) and therefore polar/hydrophilic material coated with heparan sulfate according to the subject method can be used for detection of the HIV virus. Diagnostic devices which can be linked to nucleic acid and/or glycosaminoglycans using the method according to the invention include cover slips, microarrays and beads and strips consisting of or comprising the linked polar/hydrophilic materials according to the invention.

In addition, the method in any of the embodiments or any combination of the embodiments disclosed above is applicable for any medical device that needs to be linked to nucleic acid and/or glycosaminoglycan. Medical devices which can be linked to nucleic acid and/or glycosaminoglycans using the method according to the invention include needles, guidewires, surgical instruments, catheters including balloon and jet-lysis catheters. Medical implant devices according to the invention include stents such as iliac, femoral, aortic, ureteric, biliary, tip and reduction stents, canullas, prosthetic devices such as artificial joints, heart valves, fixation, cosmetic implants, devices, delivery devices drainage devices, lenses, contact lenses, dental materials, intraoccular devices and the like.

A preferred medical device is a metal-based stent. Metal-based stents are mechanical devices whose primary function is to keep biological vessels, for example blood vessels, in an open state. They are surgically implanted to alleviate problems associated with obstructed vessels such as obstructed arteries and veins. Upon implantation, stents may attract thrombocytes (blood platelets) which induce neointima formation (intimal hyperplasia). These events lead to occlusion of such vessels that, in turn, can necessitate further surgical intervention. In order to reduce the occlusion at the site of implantation of stents, these medical devices can be coated with heparin, a glycosaminoglycan with strong anti-coagulant properties. Thus, metal-based stents can be coated with heparin, or heparan sulfate for example, with the method according to the invention. In a preferred embodiment of the invention, said metal-based stent is a stent that is based on nickel-titanium as described in Schuerch, H. U. Certain physical properties and applications of nitinol., NASA CR-1232, NASA, November 1968 and Duerig, T. W., Pelton, A. R. and Stöckel, D. Superelastic nitinol for medical devices., Medical Plastics and Biomaterials, March/April, 1997, for example. Stents according to the invention include stents which can be implanted as arterial, venous, esophageal, urological, rectal and gastrointestinal stents.

Heparin (and analogues) are potent binders of growth factors and other heparin binding proteins and capable of forming a depots of releasable factors in the body. It was investigated if heparin bound to stents is capable of binding growth factors. For this the growth factor basic fibroblast growth factor (bFGF) was used. However, heparin binding proteins which can be bound to heparin according to the invention include growth factors such as fibbroblast growth factors like acidic FGF (aFGF), vascular endothelial growth factors (VEGF), transforming growth factors, platelet-derived growth factors, kepatocyte growth factors, and epidermal growth factors, low and very low density lipoproteins and apolipoproteins, seine protease inhibitors, nucleases, polymerases, topoisomerases, oxidases, synthases, dismutases, proteases, esterases, carbohydrate hydrolases, eliminases, transferases, phosphatases, kinases, lipolytic enzymes, extracellular matrix proteins such as collagens, fibronectin, laminin, thrombospondin, vitronectin, receptor proteins such as steroid receptors, growth factor receptors and channel proteins, viral coat proteins from HIV HSV and Dengue viruses, nuclear proteins such as histones, transcription factors, prion proteins, amyloid proteins and fibrin.

In addition, stents or other medical devices which are linked to radioactive nucleic acids can be used to deliver radioactive compounds to a speicific site in the body for radiological treatment of diseases such as various forms of cancer.

It is possible to produce polar/hydrophilic materials with nucleic acid and/or glycosaminoglycan linked thereto which can be maintained for a long time and in a dried form. A long time implies a period of 2 months or more, preferably one or more years. The linked molecules above all remain bioactive, i.e. can still bind specific antibodies and undergo hybridization tests because the binding sites required therefore are not involved in the linkage to the polar/hydrophilic material.

A further advantage of diagnostic devices with such material according to the invention is that lower background values are obtained which is important in work with unpurified sera or in hybridization experiments with nucleic acids for example. In the subject method sufficient material is linked to render tests extremely sensitive. As a further advantage it can be mentioned that the polar/hydrophilic material linked to nucleic acid and/or glycosaminoglycan according to the invention is compatible with most detection systems that are current used such as by means of radioactivity, enzyme markers, fluorescent markers and chemoluminescent markers.

EXAMPLES

A number of embodiments of the subject invention are described below. While many of the examples are carried out with a polar/hydrophilic material in the shape of a stent, the examples should not be interpreted as limiting the invention to stents as such.

Section 1. Coating Stents with Heparin or Heparin Derivatives Using Different High Salt Solutions Stents (nickel-titanium; Nitanol®) were incubated with various solutions containing heparin or heparan sulfate. The amount of heparin bound to the stent was evaluated by several means:
1) immunochemically using an antibody specifically reacting with heparin
2) radiometrically using [35S]-heparin
3) enzymatically (using a bioassay)

Example 1a
Coating Various Materials with Heparin

The glass, polystyrene plastic, Nitanol® (nickel-titanium alloy), tantalum and stainless steel used in the example were cleaned with acetone for 2 hours before use, cut into 1 cm$^2$ and the weight and area of the materials were determined. The materials were placed into contact with either 1.5 ml 90% $(NH_4)_2SO_4$, or 1.5 ml PBS (phosphate buffered saline) with or without 10 mg heparin for 17 hours at 22° C. The materials were then washed 3 times with 3 ml TBST (Tris-buffered salt solution with 0.1% Teewn® 20). Subsequently, the materials were blocked with 1% BSA (bovine serum albumin)/TBST for about 30 min and then incubated with anti-heparin antibody (1:30 dilution in 1% BSA/TBST) for 1.5 h at 22° C. The materials were then washed with 3 ml TBST and incubated with a second antibody (anti-c-Myc; 1:1 dilution in 1% BSA/TBST; 9E10 mouse monoclonal antibody) for 1.5. The materials were then washed with 3 ml TBST and incubated with a third antibody (rabbit anti-mouse Ig-AP for 1 h at 22° C. The materials were again washed with 3 ml TBST. The materials were then incubated with 2 ml of 1 mg 4-nitrophenyl phosphate disodium salt/ml 1M diethanolamine, pH 9.8, 0.5 mM $MgCl_2$. This produces a yellow color in the solution which can be detected and was measured at 405 nm after 90 min.

The results are presented in FIG. 1 and Table 1a.

TABLE 1a

| | material | treatment | weight (mg) | area (cm$^2$) | E405 (100 min.) | E405/cm$^2$ | average E405/cm$^2$ |
|---|---|---|---|---|---|---|---|
| G1 | glass | 90% $(NH_4)_2SO_4$ | 32.00 | 1.79 | 0.110 | 0.061 | 0.079 |
| G2 | glass | 90% $(NH_4)_2SO_4$ | 24.10 | 1.35 | 0.130 | 0.096 | |
| G3 | glass | 90% $(NH_4)_2SO_4$ + hep | 25.80 | 1.45 | 1.302 | 0.900 | 1.018 |
| G4 | glass | 90% $(NH_4)_2SO_4$ + hep | 18.20 | 1.02 | 1.159 | 1.136 | |
| G5 | glass | PBS | 27.00 | 1.51 | 0.151 | 0.100 | 0.087 |
| G6 | glass | PBS | 33.00 | 1.85 | 0.136 | 0.073 | |
| G7 | glass | PBS + hep | 19.40 | 1.09 | 0.141 | 0.130 | 0.133 |
| G8 | glass | PBS + hep | 15.70 | 0.88 | 0.120 | 0.136 | |
| P1 | plastic* | 90% $(NH_4)_2SO_4$ | 21.40 | 1.57 | 0.093 | 0.059 | 0.065 |
| P2 | plastic* | 90% $(NH_4)_2SO_4$ | 25.80 | 1.90 | 0.136 | 0.072 | |
| P3 | plastic* | 90% $(NH_4)_2SO_4$ | 23.70 | 1.74 | 0.114 | 0.065 | |
| P4 | plastic* | 90% $(NH_4)_2SO_4$ + hep | 23.60 | 1.74 | 1.075 | 0.619 | 0.587 |
| P5 | plastic* | 90% $(NH_4)_2SO_4$ + hep | 20.80 | 1.53 | 0.851 | 0.556 | |
| P6 | plastic* | PBS | 23.20 | 1.71 | 0.101 | 0.059 | 0.057 |
| P7 | plastic* | PBS | 29.00 | 2.13 | 0.109 | 0.051 | |
| P8 | plastic* | PBS | 22.50 | 1.66 | 0.103 | 0.062 | |
| P9 | plastic | PBS + hep | 23.30 | 1.71 | 0.422 | 0.246 | 0.244 |
| P10 | plastic | PBS + hep | 24.90 | 1.83 | 0.444 | 0.242 | |
| N1 | nitinol | 90% $(NH_4)_2SO_4$ | 72.80 | 1.15 | 0.087 | 0.076 | 0.067 |
| N2 | nitinol | 90% $(NH_4)_2SO_4$ | 95.10 | 1.50 | 0.088 | 0.059 | |
| N3 | nitinol | 90% $(NH_4)_2SO_4$ | 84.50 | 1.33 | 0.089 | 0.067 | |
| N4 | nitinol | 90% $(NH_4)_2SO_4$ + hep | 100.00 | 1.58 | 1.047 | 0.663 | 0.639 |
| N5 | nitinol | 90% $(NH_4)_2SO_4$ + hep | 94.60 | 1.49 | 0.945 | 0.632 | |
| N6 | nitinol | 90% $(NH_4)_2SO_4$ + hep | 85.60 | 1.35 | 0.842 | 0.623 | |
| N7 | nitinol | PBS | 81.70 | 1.29 | 0.107 | 0.083 | 0.079 |
| N8 | nitinol | PBS | 99.80 | 1.58 | 0.112 | 0.071 | |
| N9 | nitinol | PBS | 79.30 | 1.25 | 0.103 | 0.082 | |
| N10 | nitinol | PBS + hep | 109.30 | 1.73 | 0.235 | 0.136 | 0.122 |
| N11 | nitinol | PBS + hep | 112.00 | 1.77 | 0.177 | 0.100 | |
| N12 | nitinol | PBS + hep | 105.30 | 1.66 | 0.216 | 0.130 | |

TABLE 1a-continued

| | material | treatment | weight (mg) | area (cm$^2$) | E405 (100 min.) | E405/cm$^2$ | average E405/cm$^2$ |
|---|---|---|---|---|---|---|---|
| T1 | tantalum, e438 | 90% (NH$_4$)$_2$SO$_4$ | 41.60 | 1.03 | 0.097 | 0.094 | 0.098 |
| T2 | tantalum | 90% (NH$_4$)$_2$SO$_4$ | 45.20 | 1.12 | 0.116 | 0.104 | |
| T3 | tantalum | 90% (NH$_4$)$_2$SO$_4$ | 42.80 | 1.06 | 0.102 | 0.097 | |
| T4 | tantalum | 90% (NH$_4$)$_2$SO$_4$ + hep | 42.60 | 1.05 | 0.655 | 0.623 | 0.626 |
| T5 | tantalum | 90% (NH$_4$)$_2$SO$_4$ + hep | 43.20 | 1.07 | 0.680 | 0.638 | |
| T6 | tantalum | 90% (NH$_4$)$_2$SO$_4$ + hep | 44.10 | 1.09 | 0.674 | 0.619 | |
| T7 | tantalum | PBS | 40.70 | 1.00 | 0.096 | 0.096 | 0.082 |
| T8 | tantalum | PBS | 50.30 | 1.24 | 0.100 | 0.081 | |
| 79 | tantalum | PBS | 58.70 | 1.45 | 0.100 | 0.069 | |
| T10 | tantalum | PBS + hep | 43.40 | 1.07 | 0.204 | 0.190 | 0.187 |
| T11 | tantalum | PBS + hep | 40.40 | 1.00 | 0.197 | 0.197 | |
| T12 | tantalum | PBS + hep | 52.10 | 1.29 | 0.221 | 0.172 | |
| S1 | stainless steel | 90%(NH$_4$)$_2$SO$_4$ | 756.70 | 2.08 | 0.188 | 0.090 | 0.087 |
| S2 | stainless steel | 90%(NH$_4$)$_2$SO$_4$ | 761.00 | 2.09 | 0.196 | 0.094 | |
| S3 | stainless steel | 90%(NH$_4$)$_2$SO$_4$ | 761.50 | 2.09 | 0.164 | 0.078 | |
| S4 | stainless steel | 90%(NH$_4$)$_2$SO$_4$ + hep | 758.80 | 2.09 | 1.220 | 0.585 | 0.578 |
| S5 | stainless steel | 90%(NH$_4$)$_2$SO$_4$ + hep | 756.10 | 2.08 | 1.185 | 0.570 | |
| S6 | stainless steel | 90%(NH$_4$)$_2$SO$_4$ + hep | 755.00 | 2.08 | 1.201 | 0.579 | |
| S7 | stainless steel | PBS | 749.20 | 2.06 | 0.188 | 0.091 | 0.091 |
| S8 | stainless steel | PBS | 762.60 | 2.10 | 0.200 | 0.095 | |
| S9 | stainless steel | PBS | 742.90 | 2.04 | 0.174 | 0.085 | |
| S10 | stainless steel | PBS + hep | 747.40 | 2.05 | 0.305 | 0.148 | 0.123 |
| S11 | stainless steel | PBS + hep | 743.20 | 2.04 | 0.162 | 0.079 | |
| S12 | stainless steel | PBS + hep | 759.00 | 2.09 | 0.298 | 0.143 | |

*plastic used was polychlorotrifluoroethylene

Example 1b
Coating Various Metals with Heparan Sulfate

Various metals were incubated with 1 μg heparan sulfate (a heparin analogue)/ml 90% (NH$_4$)$_2$SO$_4$ as in example 1a. The heparan sulfate bound was detected by immunochemistry using an antibody against heparan sulfate and the reuslts are shown in Table 1b.

TABLE 1b

| Material | Heparan sulfate bound/cm$^2$ |
|---|---|
| Ni/Ti (stent) | 285* |
| tantalum | 684 |
| aluminum | 371 |
| Plastic* | 100 |

*the amount of heparan sulfate bound is expressed as the percentage of the amount of heparan sulfate bound to polystyrene (a plastic) which is take as 100%

Example 2
Binding of Heparin to Stents Using High Salt Solutions and Detection by Immunochemistry were incubated in 1.5 ml solutions containing 10 μg heparin/ml for 17 h at 22° C. After washing in 5×2 ml distilled water, stents were incubated with a 2 ml solution containing anti-heparin antibodies which were subsequently visualized using 2 ml of a solution containing alkaline phosphatase-conjugated antibodies reactive with the anti-heparin antibodies. The amount of alkaline phosphatase bound was evaluated by adding a 2 ml of 1 mg/ml chromogenic substrate (p-nitrophenylphosphate) and spectrophotometric detection of the p-nitrophenol formed. The amount of p-nitrophenol is a measure of the amount of heparin bound to the stents. The following solutions were analyzed: H$_2$O, PBS (phosphate buffered saline, which contains about 0.9% NaCl), 90% NaCl and 90% (NH$_4$)$_2$SO$_4$, and the results are presented in Table 2.

TABLE 2

Binding of heparin to stents using high salt solutions.

| Solution | Stent weight (mg) | Absorbance at 405 nm | A405/ g stent |
|---|---|---|---|
| 10 μg heparin/ml H$_2$O | 25 | 0.002 | 0.08 |
| 10 μg heparin/ml PBS | 32 | 0.000 | 0 |
| 10 μg heparin/ml 90% NaCl | 27 | 0.475 | 17.59 |
| 10 μg heparin/ml 90% (NH$_4$)$_2$SO$_4$ | 29 | 1.078 | 37.17 |

Example 3

Binding of Heparin to Stents Using High Salt Solutions and Detection by Radiometry Stents were incubated in various heparin-containing solutions (see above) for 17 h at 22° C. (Table 3a), or for 8 h at 80° C. (Table 3b). Stents were washed in distilled water until no radioactivity could be detected in the washing fluid. The amount of radioactivity was detected in a liquid scintillation analyzer and is expressed as disintegrations per minute.

TABLE 3a

Binding of heparin to stents incubated in various heparin-containing solutions for 17 h at 22° C.

| Solution | Stent weight (mg) | dpm**/stent | Dpm*/mg stent |
|---|---|---|---|
| 128* μg heparin/ml H$_2$O | 51 | 571 | 11.2 |
| 128 μg heparin/ml PBS | 47 | 739 | 15.7 |
| 128 μg heparin/ml 90% NaCl | 48 | 507 | 10.6 |
| 128 μg heparin/ml 90% (NH$_4$)$_2$SO$_4$ | 48 | 2574 | 53.6 |

*6.5 μg [$^{35}$S] – heparin + 121.5 μg unlabeled heparin
**dpm: disintegrations per minute TABLE 3b Binding of heparin to stents incubated in
various heparin-containing solutions for 8 H at 80° C.

| Solution | Stent weight (mg) | dpm*/ stent | dpm*/ weight |
|---|---|---|---|
| 10 μg [35S]-heparin/ml H₂O | 45 | 331 | 7.4 |
| 10 μg [35S]-heparin/ml PBS | 48 | 318 | 6.6 |
| 10 μg [35S]-heparin/ml 90% NaCl | 51 | 1986 | 38.5 |
| 10 μg [35S]-heparin/ml 90% (NH₄)₂SO₄ | 49 | 5554 | 113.3 |

*dpm: disintegrations per minute

Binding of [$^{35}$S]-heparin to stents was also evaluated by autoradiography. For this stents were incubated in 1.5 ml of 90% (NH$_4$)$_2$SO$_4$ containing 0, 5, 10 and 20 μg [$^{35}$S]-heparin, washed, and placed on a X-ray film for 3 days (see FIG. 1).

Example 4
Binding of Heparin to Stents Using High Salt Solutions and Detection by Potentiation of Anti Thrombin III (Bioassay)

Stents were incubated in various solutions for 17 h at 22° C., and washed in distilled water. They were then incubated with a solution containing anti-thrombin III followed by addition of Factor Xa and its chromogenic substrate. This assay is based on the potentiation by heparin of the inhibitory capacity of anti-thrombin III towards the protease Factor Xa. An increase of the inhibitory capacity of anti-thrombin III results in a reduction of the amount of chromogenic substrate cleaved by Factor Xa. The chromophoric product is measured at 405 nm. The experiment was performed according to the manufacture's instruction (Sigma diagnostics, procedure No. CRS 106) and the results are shown in Table 4. The amount of bioactive heparin can be deduced by comparison with a calibration curve.

TABLE 4

Binding of heparin to stents using high salt solutions and
detection by potentiation of anti thrombin III (bioassay)

| Solution | Stent weight (mg) | μg bioactive heparin/gram stent |
|---|---|---|
| 10 mg heparin/ml H2O | 30 | 0 |
| 10 mg heparin/ml PBS | 27 | 0 |
| 10 mg heparin/ml 90% NaCl | 28 | 0.2 |
| 10 mg heparin/ml 90% (NH₄)₂SO₄ | 30 | 0.5 |

Example 5
Optimal Concentration of (NH$_4$)$_2$SO$_4$

Stents were incubated with various amounts of [$^{35}$S]-heparin in (NH$_4$)$_2$SO$_4$ for 17 h at 22° C. Stents were washed in distilled water until no radioactivity could be detected in the washing fluid. The amount of radioactivity was detected in a liquid scintillation analyzer and is expressed as disintegrations per minute in Table 5.

TABLE 5

| Solution | Stent weight (mg) | dpm*/ stent | Dpm/mg stent |
|---|---|---|---|
| 10 μg [35S]-heparin/ml H₂O | 43.0 | 662 | 15.4 |
| 10 μg [35S]-heparin/ml 25% (NH₄)₂SO₄ | 37.5 | 1373 | 36.6 |
| 10 μg [35S]-heparin/ml 50% (NH₄)₂SO₄ | 37.5 | 1551 | 41.4 |
| 10 μg [35S]-heparin/ml 60% (NH₄)₂SO₄ | 45.5 | 1459 | 32.1 |

TABLE 5-continued

| Solution | Stent weight (mg) | dpm*/ stent | Dpm/mg stent |
|---|---|---|---|
| 10 μg [35S]-heparin/ml 70% (NH₄)₂SO₄ | 40.0 | 1713 | 42.8 |
| 10 μg [35S]-heparin/ml 80% (NH₄)₂SO₄ | 47.5 | 2300 | 48.4 |
| 10 μg [35S]-heparin/ml 90% (NH₄)₂SO₄ | 41.0 | 2841 | 69.3 |
| 10 μg [35S]-heparin/ml 100% (NH₄)₂SO₄ | 45.0 | 3343 | 74.3 |

Example 6
Reduction of Platelet Adhesion to Stents Coated with Heparin

Blood was obtained by venipuncture of healthy adults. Sodium citrate was added to 3.8%. This was centrifuged for 15 min at 1100 rpm. The supernatant contains human platelet-rich plasma. Stents were coated with heparin for 17 h, 22° C., and incubated in human platelet-rich plasma for 30 min at 22° C. After washing in Hanks balanced salt solution (Gibco BRL), the amount of platelets attached to the stent was evaluated by analysis of the amount of lactate dehydrogenase released from the platelets after lysis in 1% Triton X-100 ("Biochemical Information", Boehringer Mannheim GmbH, 1973, pp 121–122). The results of this experiment are given in Table 6.

TABLE 6

| Solution | number of thrombocytes/l | lactate dehydrogenase (arbitrary units) |
|---|---|---|
| 0 mg heparin/ml 90% (NH₄)₂SO₄ | 454 × 10⁹ | 78 |
| 10 mg heparin/ml 90% (NH₄)₂SO₄ | 454 × 10⁹ | 42 |
| 0 mg heparin/ml 90% (NH₄)₂SO₄ | 114 × 10⁹ | 64 |
| 10 mg heparin/ml 90% (NH₄)₂SO₄ | 114 × 10⁹ | 14 |

Example 7
Use of Stent-Bound Heparin as Vehicle for Growth Factors

Heparin(analogues) are potent binders of growth factors and capable of forming a depots of growth factors in the body. It was investigated if heparin bound to stents is capable of binding growth factors. For this the growth factor basic fibroblast growth factor (bFGF) was used.

Stents were coated with or without heparin for 17 h, 22° C. in 90% (NH$_4$)$_2$SO$_4$. After washing, stents were incubated in a solution containing 5 μg bFGF/ml PBS. After washing, bFGF was detected by immunochemistry using anti-bFGF antibodies and alkaline phosphatase-conjugated antibodies reactive with the anti-bFGF antibodies. The amount of alkaline phosphatase bound was evaluated by adding a chromogenic substrate (p-nitrophenylphosphate) and spectrophotometric detection of the p-nitrophenol formed. The amount of p-nitrophenol formed is a measure of the amount of bFGF bound to the stents and the results of this experiment are shown in Table 7.

TABLE 7

Use of heparin-coated stents as vehicles for growth factors

| Solution | absorption at 405 nm/ gram stent | Stent weight (mg) |
|---|---|---|
| 90% (NH₄)₂SO₄ | 0 | 26 |
| 10 mg heparin/ml 90% (NH₄)₂SO₄ | 0 | 27 |

TABLE 7-continued

Use of heparin-coated stents as vehicles for growth factors

| Solution | absorption at 405 nm/ gram stent | Stent weight (mg) |
|---|---|---|
| 90% (NH$_4$)$_2$SO$_4$ + bFGF | 11 | 32 |
| 10 mg heparin/ml 90% (NH$_4$)$_2$SO$_4$ + bFGF | 20 | 28 |

Section II. Coating Stent with DNA Using High Salt Solutions

Example 8

Coating with DNA Using High Salt Solutions

DNA (deoxyribonucleic acid (pUC 119 plasmid) was labeled with [$^{32}$]P by random priming. Stents were incubated in the various solutions for 17 h at 22° C., and washed in distilled water until no radioactivity could be detected in the washing fluid. The amount of radioactivity was detected in a liquid scintillation analyzer and is expressed as disintegrations per minute. The amount of DNA bound was calculated from the specific activity of the labeled DNA (Table 8).

TABLE 8

Binding of DNA (deoxyribonucleic acid) to stents using high salt solutions and radiometrical detection

| Solution | Stent weight (mg) | dpm*/stent | μg DNA/ g stent |
|---|---|---|---|
| 10 μg* DNA/1.5 ml H$_2$O | 22.15 | 547 | 0.0 |
| 10 μg DNA/1.5 ml PBS | 33.40 | 3137 | 0.5 |
| 10 μg DNA/1.5 ml 90% NaCl | 31.50 | 29175 | 5.4 |
| 10 μg DNA/1.5 ml 90% (NH$_4$)$_2$SO$_4$ | 29.15 | 124037 | 24.8 |

*100 ng [$^{32}$P]-double strand (ds) DNA + 10 μg unlabeled ds DNA.

Figure 2:
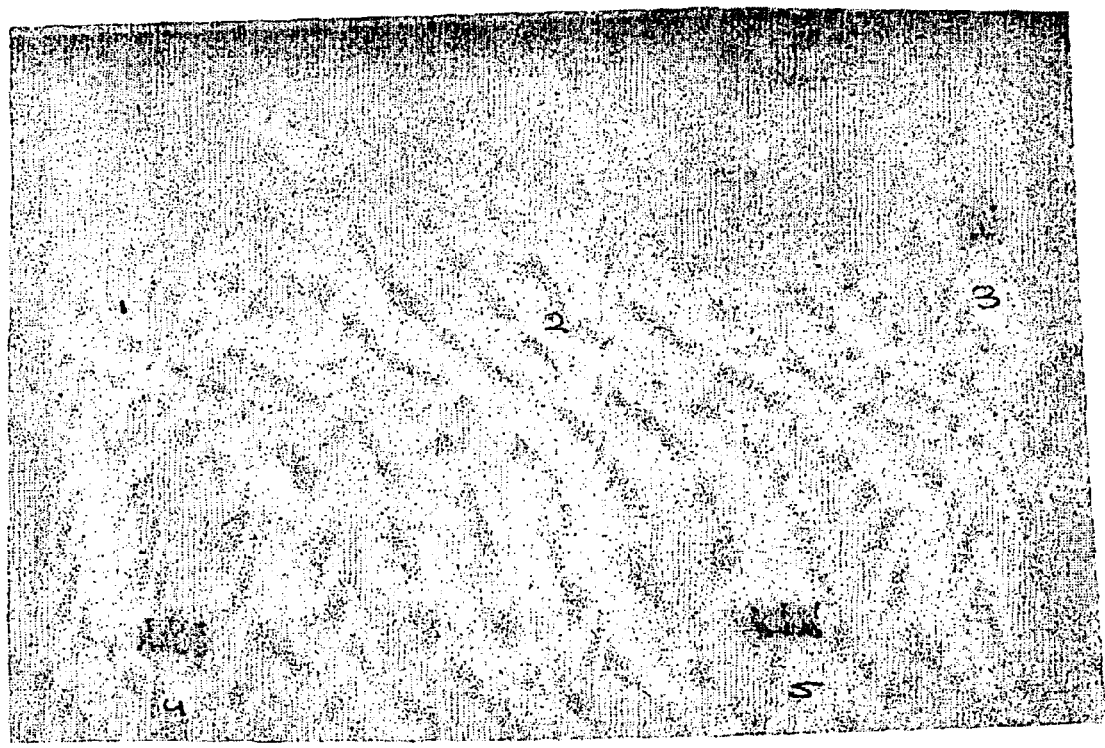
FIG. 2. Autoradiogram of stents coated with [$^{35}$S]-heparin. Stents are depicted as 1 to 5 which were treated as follows: stent 1: 1.5 ml 90% $(NH_4)_2SO_4$; stent 2: 1.5 ml 90% $(NH_4)_2SO_4$; stent 3: 1.5 ml 90% $(NH_4)_2SO_4$+5 µg 35-S heparin; stent 4: 1.5 ml 90% $(NH_4)_2SO_4$+10 µg 35-S heparin; stent 5: 1.5 ml 90% $(NH_4)_2SO_4$+20 µg 35-S heparin.
Figure 3:
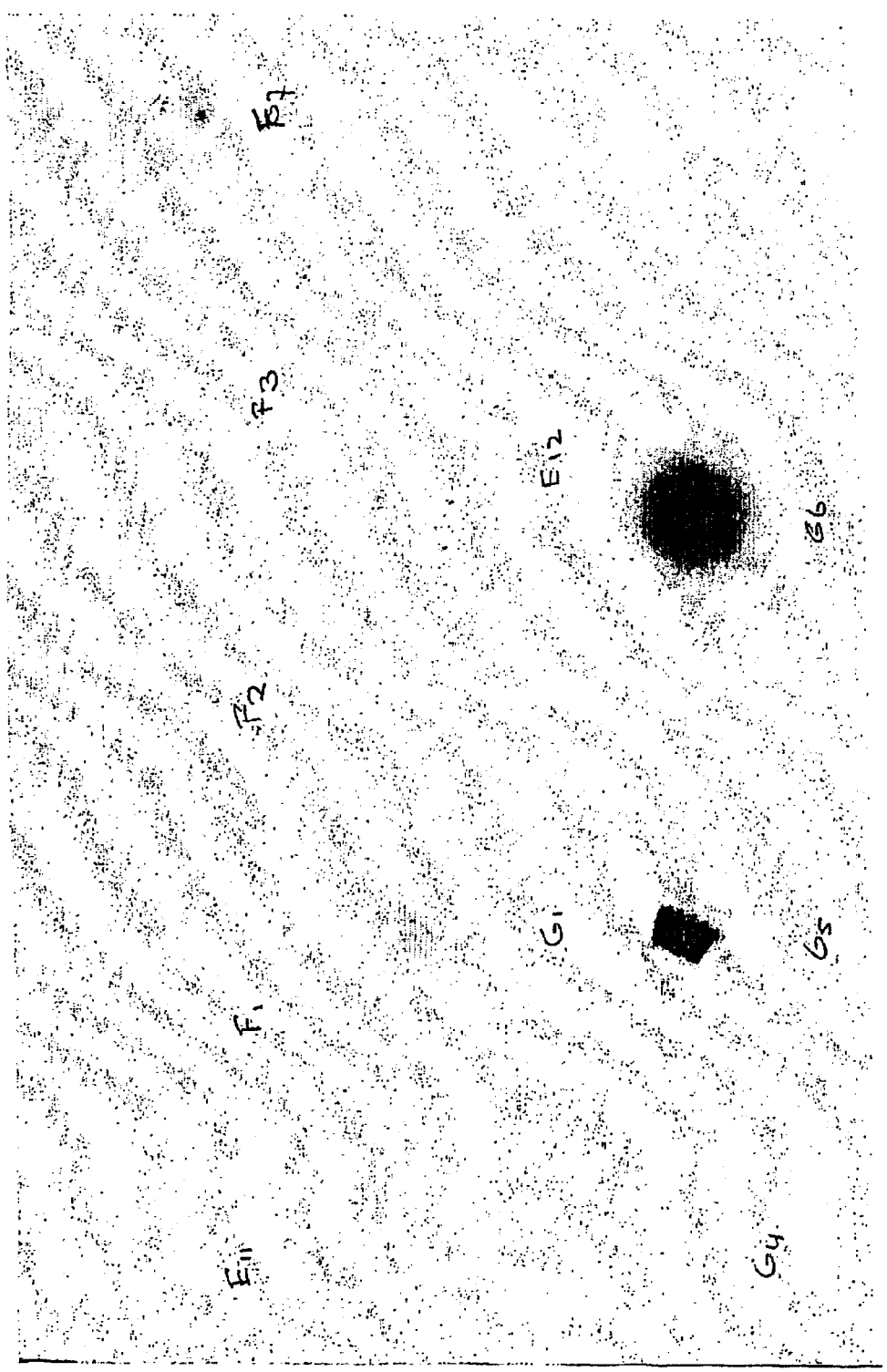
FIG. 3. Autoradiogram of stents coated with [$^{32}$P]-DNA. After washing, stents were placed on a x-ray film for 1 and 3 days (see FIG. 2). Depicted stents were treated as follows: stents E11, E12 and F1: 1.5 ml $H_2O$; stents F2 and F3: 1.5 ml PBS; stents F7 and G1: 1.5 ml 90% NaCl+32-P DNA; stent G4: 1.5 ml 90% $(NH_4)_2SO_4$; stents G5 and G6: 1.5 ml 90% $(NH_4)_2O_4$+32-P DNA.

Binding of [$^{32}$]P-DNA to stents was also evaluated by autoradiography (FIG. 2). For experimental details see above. After washing, stents were placed on a x-ray film for 1 and 3 days (see FIGS. 2a and 2b).

Example 9

Bioavailability of DNA (Deoxyribonucleic Acid) Bound to Stents

To investigate if the DNA bound to stents is bioavailable, an experiment was performed to evaluated if a DNA cutting enzyme (DNAse I, bovine pancrease, grade II, Boehringer Mannheim) is able to digest stent-coated DNA. Stents were incubated in buffer solutions with or without DNA-se. Stents were incubated with 100 ng (32-P)-dsDNA and 10 μg unlabeled dsDNA for 17 hours at 22° C. in 90% (NH$_4$)$_2$SO$_4$. After washing, the stents were incubated in 1.5 ml buffer (50 mM KCl, 10 mM Tris, 1.5 mM CaCl$_2$) containing 2 μl of 10 mg/ml DNAse for 20 min at 37° C. After DNAse treatment, stents were washed 5 times with distilled water and the amount of radioactivity bound to the stents was detected in a liquid scintillation analyzer. Table 9 indicates that about 58% of the DNA has been cleaved off from the stent. The accessibility of the DNA towards the enzyme indicates the bioavailability of the DNA bound. This is of importance for biological interactions such as hybridization.

TABLE 9

| Solution | dpm*/stent | μg DNA/g stent |
|---|---|---|
| 10 μg DNA/1.5 ml 90% (NH$_4$)$_2$SO$_4$: no DNAse treatment | 23868 | 24.8 |
| 10 μg DNA/1.5 ml 90% (NH$_4$)$_2$SO$_4$: DNAse treatment: | 9964 | 10.5 |

What is claimed:

1. A method for linking one of a nucleic acid, a glycosaminoglycan and a glycosaminoglycan mimetics to a polar/hydrophilic material of one of a medical device and a medical implant, comprising the step of contacting one of a nucleic acid, a glycosaminoglycan and a glycosaminoglycan mimetic with a polar/hydrophilic material in a solution that is 20 to 100 percent saturated with a non-chaotropic salt to produce a coated polar/hydrophilic material.

2. The method of claim 1, further comprising the step of removing the solution from the coated polar/hydrophilic material.

3. The method of claim 2, further comprising, after the step of removing the solution from the coated polar/hydrophilic material, the step of rinsing the coated polar/hydrophilic material with one of water, a buffered solution, a salt solution and buffered salt solution.

4. The method of claim 1, wherein the solution is at least 70 percent saturated with the non-chaotropic salt.

5. The method of claim 1, wherein the solution is at least 90 percent saturated with the non-chaotropic salt.

6. The method of claim 1, wherein the solution is 100 percent saturated with the non-chaotropic salt.

7. The method of claim 1, wherein the non-chaotropic salt is a salt selected from the group consisting of a non-chaotropic salt of the Hofmeister series of salts, a salt of a metal of group I or II of the Periodic Table of Elements and an NH$_4$ salt.

8. The method of claim 1, wherein the non-chaotropic salt is (NH$_4$)$_2$SO$_4$.

9. The method of claim 1, wherein the solution has a pH of about 0 to 8.

10. The method of claim 9, wherein the solution has a pH of about 2 or less.

11. The method of claim 1, wherein the contacting step is carried out at a temperature ranging from 0° C. to 100° C.

12. The method of claim 11, wherein the contacting step is carried out at a temperature ranging from 4° C. to 80° C.

13. The method of claim 1, wherein a nucleic acid is linked to the polar/hydrophilic material.

14. The method of claim 13, wherein the nucleic acid comprises one of a single stranded DNA, double stranded DNA and RNA.

15. The method of claim 1, wherein one of a glycosaminoglycan and a glycosaminoglycan mimetic is linked to the polar/hydrophilic material.

16. The method of claim 15, further comprising the step of binding a growth factor to the coated polar/hydrophilic material.

17. The method of claim 16, wherein the growth factor is bFGF, aFGF or VEGF or a combination thereof.

18. The method of claim 1, wherein one of hepann and heparan sulfate is linked to the polar/hydrophilic material.

19. The method of claim 1, wherein the medical device or implant is a stent.

20. The method of claim 19, wherein the stent comprises a nickel-titanium alloy.

21. A medical device or implant prepared according to the process of claim 1.

22. A stent prepared according to the process of claim 1.

23. The stent of claim 22, comprising a nickel-titanium alloy.

24. A method for linking one of a nucleic acid, a glycosaminoglycan and a glycosaminoglycan mimetics to a polar/hydrophilic material, comprising the step of contacting one of a nucleic acid, a glycosaminoglycan and a glycosaminoglycan mimetic with a polar/hydrophilic material in a solution that is 20 to 100 percent saturated with a non-chaotropic salt to produce a coated polar/hydrophilic material, wherein the hydrophilic material is one of a metal, a ceramic and a glass.

25. The method of claim 24, further comprising the step of removing the solution from the coated polar/hydrophilic material.

26. The method of claim 25, further comprising, after the step of removing the solution from the coated polar/hydrophilic material, the step of rinsing the coated polar/hydrophilic material with one of water, a buffered solution, a salt solution and buffered salt solution.

27. The method of claim 24, wherein the solution is at least 70 percent saturated with the non-chaotropic salt.

28. The method of claim 24, wherein the solution is at least 90 percent saturated with the non-chaotropic salt.

29. The method of claim 24, wherein the solution is 100 percent saturated with the non-chaotropic salt.

30. The method of claim 24, wherein the non-chaotropic salt is a salt selected from the group consisting of a non-chaotropic salt of the Hofmeister series of salts, a salt of a metal of group I or II of the Periodic Table of Elements and an $NH_4$ salt.

31. The method of claim 24, wherein the non-chaotropic salt is $(NH_4)_2SO_4$.

32. The method of claim 24, wherein the solution has a pH of about 0 to 8.

33. The method of claim 32, wherein the solution has a pH of about 2 or less.

34. The method of claim 24, wherein the contacting step is carried out at a temperature ranging from 0° C. to 100° C.

35. The method of claim 34, wherein the contacting step is carried out at a temperature ranging from 4° C. to 80° C.

36. The method of claim 24, wherein a nucleic acid is linked to the polar/hydrophilic material.

37. The method of claim 36, wherein the nucleic acid comprises one of a single stranded DNA, double stranded DNA and RNA.

38. The method of claim 24, wherein one of a glycosaminoglycan and a glycosaminoglycan mimetic is linked to the polar/hydrophilic material.

39. The method of claim 38, further comprising the step of binding a growth factor to the coated polar/hydrophilic material.

40. The method of claim 39, wherein the growth factor is bFGF, aFGF or VEGF or a combination thereof.

41. The method of claim 24, wherein one of heparin and heparan sulfate is linked to the polar/hydrophilic material.

42. The method of claim 24, wherein the polar/hydrophilic material is a stent.

43. The method of claim 42, wherein the stent comprises a nickel-titanium alloy.

44. A coated polar/hydrophilic material prepared according to the process of claim 24.

45. A method for linking one of a nucleic acid, a glycosaminoglycan and a glycosaminoglycan mimetics to a polar/hydrophilic material, comprising the step of contacting one of a nucleic acid, a glycosaminoglycan and a glycosaminoglycan mimetic with a polar/hydrophilic material in a solution that is 20 to 100 percent saturated with a non-chaotropic salt to produce a coated polar/hydrophilic material, wherein the non-chaotropic salt is an $NH_4$ salt.

46. The method of claim 45, further comprising the step of removing the solution from the coated polar/hydrophilic material.

47. The method of claim 46, further comprising, after the step of removing the solution from the coated polar/hydrophilic material, the step of rinsing the coated polar/hydrophilic material with one of water, a buffered solution, a salt solution and buffered salt solution.

48. The method of claim 45, wherein the solution is at least 70 percent saturated with the non-chaotropic salt.

49. The method of claim 45, wherein the solution is at least 90 percent saturated with the non-chaotropic salt.

50. The method of claim 45, wherein the solution is 100 percent saturated with the non-chaotropic salt.

51. The method of claim 45, wherein the non-chaotropic salt is $(NH_4)_2SO_4$.

52. The method of claim 45, wherein the solution has a pH of about 0 to 8.

53. The method of claim 52, wherein the solution has a pH of about 2 or less.

54. The method of claim 45, wherein the contacting step is carried out at a temperature ranging from 0° C. to 100° C.

55. The method of claim 54, wherein the contacting step is carried out at a temperature ranging from 4° C. to 80° C.

56. The method of claim 45, wherein a nucleic acid is linked to the polar/hydrophilic material.

57. The method of claim 56, wherein the nucleic acid comprises one of a single stranded DNA, double stranded DNA and RNA.

58. The method of claim 45, wherein one of a glycosaminoglycan and a glycosaminoglycan mimetic is linked to the polar/hydrophilic material.

59. The method of claim 58, further comprising the step of binding a growth factor to the coated polar/hydrophilic material.

60. The method of claim 59, wherein the growth factor is bFGF, aFGF or VEGF or a combination thereof.

61. The method of claim 45, wherein one of heparin and heparan sulfate is linked to the polar/hydrophilic material.

62. The method of claim 45, wherein the polar/hydrophilic material is a stent.

63. The method of claim 62, wherein the stent comprises a nickel-titanium alloy.

64. A coated polar/hydrophilic material prepared according to the process of claim 45.

* * * * *

UNITED STATES PATENT AND TRADEMARK OFFICE
CERTIFICATE OF CORRECTION

PATENT NO. : 6,933,379 B2
DATED : August 23, 2005
INVENTOR(S) : Antonius H.M.S.M. Van Kuppevelt et al.

It is certified that error appears in the above-identified patent and that said Letters Patent is hereby corrected as shown below:

Column 2,
Line 39, after "strongly linked to nucleic acids and/or glycosaminoglycans", insert a -- . --.
Line 51, delete "on a x-ray film" and substitute -- on an x-ray film --.
Line 56, delete "$(NH_4)_2O_4$+32-P DNA and substitute -- $(NH_4)_2SO_4$+32-P DNA. --.

Column 6,
Line 47, delete, "a depots of" and substitute -- a depot of --.

Column 9,
Line 20, delete "79 tantalum PBS" and substitute -- T9 tantalum PBS --.
Lines 45 and 46, delete "which is take as" and substitute -- which is taken as --.

Column 11,
Line 18, delete "on a x-ray" and substitute -- on an x-ray --.

Column 12,
Line 41, delete "forming a depots" and substitute -- forming a depot --.
Line 41, delete "Heparin(analogues)" and insert a space between "Heparin (analogues)".

Column 13,
Line 43, delete "on a x-ray" and substitute -- on an x-ray --.

Column 14,
Line 61, delete "wherein one of hepann and" and substitute -- wherein one of heparin and --.

Column 15,
Line 5, delete "a glycosominoglycan mimetics" and substitute -- a glycosominoglycan mimetic --.

UNITED STATES PATENT AND TRADEMARK OFFICE
CERTIFICATE OF CORRECTION

PATENT NO.    : 6,933,379 B2
DATED         : August 23, 2005
INVENTOR(S)   : Antonius H.M.S.M. Van Kuppevelt et al.

It is certified that error appears in the above-identified patent and that said Letters Patent is hereby corrected as shown below:

Column 16,
Line 6, delete "a glycosominoglycan mimetics" and substitute -- a glycosominoglycan mimetic --.

Signed and Sealed this

Fourteenth Day of March, 2006

JON W. DUDAS
*Director of the United States Patent and Trademark Office*